United States Patent
Palma et al.

(10) Patent No.: US 11,660,061 B2
(45) Date of Patent: *May 30, 2023

(54) METHOD AND SYSTEM FOR MOTION ASSESSMENT AND CORRECTION IN DIGITAL BREAST TOMOSYNTHESIS

(71) Applicant: General Electric Company, Schenectady, NY (US)

(72) Inventors: Giovanni John Jacques Palma, Buc (FR); Jorge Corsino Espino, Buc (FR); Rémy Klausz, Buc (FR); Razvan Iordache, Buc (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 133 days.

This patent is subject to a terminal disclaimer.

(21) Appl. No.: 17/207,148

(22) Filed: Mar. 19, 2021

(65) Prior Publication Data

US 2021/0204899 A1    Jul. 8, 2021

Related U.S. Application Data

(63) Continuation of application No. 15/692,992, filed on Aug. 31, 2017, now Pat. No. 10,993,689.

(51) Int. Cl.
*A61B 6/00* (2006.01)
*G06T 7/00* (2017.01)
(Continued)

(52) U.S. Cl.
CPC ............ *A61B 6/5264* (2013.01); *A61B 5/055* (2013.01); *A61B 6/025* (2013.01); *A61B 6/032* (2013.01); *A61B 6/037* (2013.01); *A61B 6/502* (2013.01); *A61B 8/481* (2013.01); *A61B 90/39* (2016.02); *G06T 5/003* (2013.01); *G06T 7/0016* (2013.01); *G06T 7/246* (2017.01); *G06T 7/248* (2017.01); *G06T 11/008* (2013.01); *A61B 2090/3908* (2016.02); *A61B 2090/3925* (2016.02); *A61B 2090/3954* (2016.02); *A61B 2090/3966* (2016.02); *G06T 2207/10112* (2013.01); *G06T 2207/20201* (2013.01);
(Continued)

(58) Field of Classification Search
CPC ................ A61B 6/5258; A61B 6/5264; G06T 2207/20201; G06T 7/0016
See application file for complete search history.

(56) References Cited

U.S. PATENT DOCUMENTS

| | | | |
|---|---|---|---|
| 6,721,387 B1 * | 4/2004 | Naidu .................. | A61B 6/5258 378/4 |
| 2007/0014452 A1 * | 1/2007 | Suresh .................. | G06T 7/0012 382/128 |

(Continued)

*Primary Examiner* — Amelie R Davis

(57) ABSTRACT

An imaging system, such as a DBT system, capable of providing an operator of the system with information concerning the location, magnitude and direction of motion detected by the system during performance of the scan to enhance image processing. The imaging system provides the motion information to the operator directly in conjunction with the images processed by the imaging system thereby providing the operator with sufficient information for decisions regarding the need for additional images for completing the scan with the imaging system before the patient is discharged, or even before the breast is decompressed.

7 Claims, 5 Drawing Sheets

(51) Int. Cl.
*G06T 11/00* (2006.01)
*A61B 6/02* (2006.01)
*A61B 6/03* (2006.01)
*A61B 8/08* (2006.01)
*A61B 90/00* (2016.01)
*G06T 7/246* (2017.01)
*G06T 5/00* (2006.01)
*A61B 5/055* (2006.01)

(52) U.S. Cl.
CPC ............... *G06T 2207/30068* (2013.01); *G06T 2207/30204* (2013.01); *G06T 2207/30241* (2013.01)

(56) References Cited

U.S. PATENT DOCUMENTS

| | | | | |
|---|---|---|---|---|
| 2007/0197907 | A1* | 8/2007 | Bruder | A61B 6/032 |
| | | | | 600/407 |
| 2010/0249592 | A1* | 9/2010 | Langeland | G06T 7/246 |
| | | | | 600/443 |
| 2012/0033868 | A1* | 2/2012 | Ren | A61B 6/025 |
| | | | | 378/21 |
| 2016/0007948 | A1* | 1/2016 | Isola | A61B 6/5258 |
| | | | | 382/131 |
| 2017/0042494 | A1* | 2/2017 | Kim | G06T 11/006 |

* cited by examiner

No patient movement

METHOD AND SYSTEM FOR MOTION ASSESSMENT AND CORRECTION IN DIGITAL BREAST TOMOSYNTHESIS

This Application is a continuation of U.S. patent application Ser. No. 15/692,992, filed Aug. 31, 2017, which application is herein incorporated by reference.

BACKGROUND OF INVENTION

X-ray screening exams are used to detect breast cancer and other diseases. Efforts to improve the sensitivity and specificity of breast x-ray systems have led to the development of tomosynthesis systems. Breast tomosynthesis is a three-dimensional imaging technology that involves acquiring images of a stationary compressed breast at multiple angles during a short scan. The individual images are reconstructed into a series of thin, high-resolution slices that can be displayed individually or in a dynamic cine mode. Reconstructed tomosynthesis slices reduce or eliminate the problems caused by tissue overlap and structure noise in single slice two-dimensional mammography imaging. Digital breast tomosynthesis also offers the possibility of reduced breast compression, improved diagnostic and screening accuracy, fewer recalls, and 3D lesion localization.

In order to facilitate screening and diagnosis with tomosynthesis systems, such as systems for conducting digital breast tomosynthesis (DBT) scans or acquisitions, it is generally desirable to obtain high quality images. One cause of degradation of image quality is patient motion during the tomosynthesis scan. Patient motion tends to cause blurring of one or more of the images. The blurring can be severe enough to render the associated images unacceptable for clinical screening or diagnosis. Any motion in DBT acquisitions may be difficult to detect and can be a real problem regarding the visibility of small objects like calcifications in reconstructed volumes/computerized images. This, motion usually results in blur and distortions of objects in the reconstructed slices, and for heavy motion, tiny structures can even be completely cancelled from the reconstructed volumes/computerized images.

Further complicating the problem, the tomosynthesis images obtained during a scan might not be analyzed until after the patient's breast has been decompressed and the patient has been discharged. As a result, the patient must be called back for a new scan due to severe image blurring, thereby increasing patient frustration and anxiety, and potentially delaying diagnosis of malignancies.

One prior solution to this problem is disclosed in Ren et. al U.S. Pat. No. 9,498,180, entitled Detecting And Quantifying Patient Motion During Tomosynthesis Scans, (the '180 patent) the entirety of which is expressly incorporated herein by reference for all purposes. In this reference, the DBT system determines the presence and magnitude of motion occurring in a DBT scan by comparing the actual positions of a distinct feature of the patient breast, such as a marker positioned on an exterior skin line, with expected positions for the distinct feature based on a computed projection path determined from the path of the imaging source relative to the distinct feature. If the actual position differs from the expected position by more than a set threshold, the DBT system provides the operator of the system with a notification of a motion score indicating that motion has occurred during the scan and the relative magnitude of the motion based on the value of the motion score. The operator can then determine based on live motion score if additional images need to be taken to complete the scan. The DBT system can additionally correct the images in which the motion was detected, such by rejection of the images including motion above the threshold in image reconstruction.

While the DBT system in the '180 patent provides an indication to the operator of the presence and relative magnitude of motion detected in the scan, this indication does not provide the operator with any further information regarding the motion, leaving the operator with only binary decision-making information (OK/not OK) from the system of the '180 patent for analyzing images based on the motion detected by the system.

Accordingly, it is desirable to provide an imaging system, such as a DBT system, with the capability to provide an operator with enhanced information regarding motion detected during a scan performed by the imaging system as well as to automatically display the enhanced information during performance of the scan, thereby improving the scan results.

BRIEF DESCRIPTION OF THE INVENTION

There is a need or desire for an imaging system, such as a DBT system, capable of providing an operator of the system with information concerning the location, magnitude and direction of motion detected by the system during performance of the scan to enhance image processing. The imaging system provides the motion information to the operator directly in conjunction with the images processed by the imaging system thereby providing the operator with sufficient information for decisions regarding the need for additional images for completing the scan with the imaging system before the patient is discharged, or even before the breast is decompressed.

According to another aspect of the invention, a method is provided including generating a plurality of images of an imaging target of an object or body, such as a patient or individual, in a time series during a scan, processing the plurality of images to generate processed images, wherein the processed images are at least one of one or more projection images or one or more derived (e.g. reconstructed) images or combinations thereof, using a computer, detecting and quantifying motion of the target of any magnitude during the scan by comparing an actual location of at least one object of interest in each processed image with an expected location of the at least one object of interest derived from a set of the processed images, wherein the at least one point of reference is an intrinsic marker of the object or body generating a motion marker indicative of the magnitude and direction of the detected motion; and displaying the motion marker in conjunction with the processed images.

According to still another aspect of the invention, an apparatus for indication and display of motion in acquired images includes an image acquisition mechanism that generates a plurality of images of an imaging target of an object or body, such as a patient or individual, in a time series during a scan, an image processor that processes the plurality of images to generate processed images, wherein the processed images are at least one of a projection image and/or a reconstructed image, a computer which is configured to display the processed images and which detects and quantifies motion of the during the scan by comparing an actual location of at least one object of interest in each processed image with an expected location of the at least one object of interest derived from a set of the processed images and by generating a motion marker; and a mechanism for displaying the motion marker in conjunction with the processed images.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OP THE DRAWINGS

The drawings illustrate the best mode presently contemplated of carrying out the disclosure. In the drawings FIG. 1 is a schematic view of an imaging system performing a scan of a patient to determine the presence of an object of interest within the patient according to an exemplary embodiment of the invention.

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
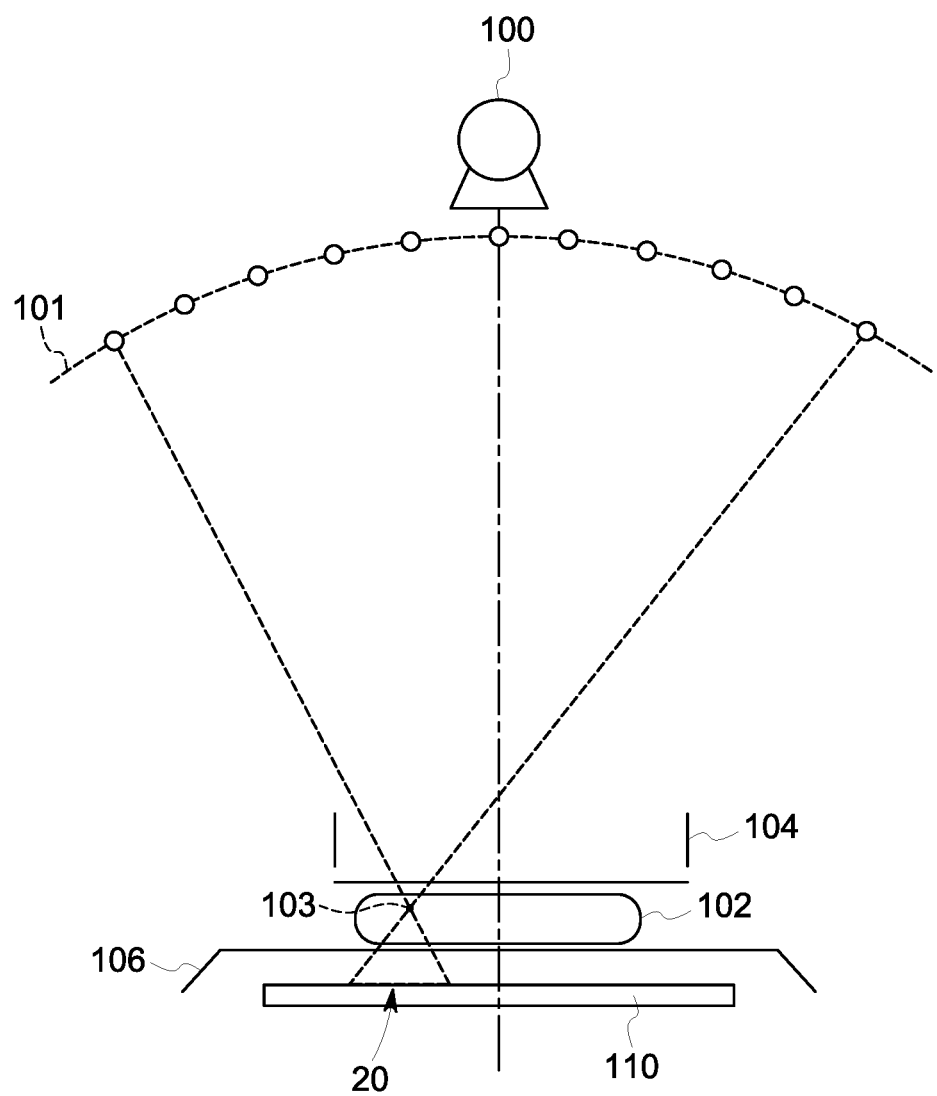

Referring to FIG. 1, during a tomosynthesis scan a patient's breast 102 is immobilized between a compression paddle 104 and a breast platform 106. An x-ray receptor 110 is disposed within a housing located below the breast platform 106. An x-ray source 100 moves along an arc 101 which may be centered on the top surface of the receptor 110. At predetermined discrete positions source 100 is energized to emit a collimated x-ray beam, for example and without limitation, at every 3° of an arc of +/−24°. The beam irradiates the breast 102, and radiation that has passed through the breast is received by receptor 110. Receptor 110 and associated electronics generate image data in digital form for each pixel of a rectangular grid of pixels at each predetermined discrete angular position of source 100.

The motion of source 100 can be continuous or discontinuous. If motion is continuous, a respective set of image data is accumulated over a small increment of continuous motion, e.g., a 0.1° to 0.5° arc of motion of source 100, although these non-limiting parameters are only an example. Different ranges of motion of the source 100 can be used, and the motion of the source 100 may be along an arc centered at a different axis, such as inside immobilized breast 102 or at breast platform 106 or at receptor 110. Furthermore, source motion is not necessarily along an arc, and can be translational or a combination of different types of motions, such as partly translational and partly rotational.

Figure 2:
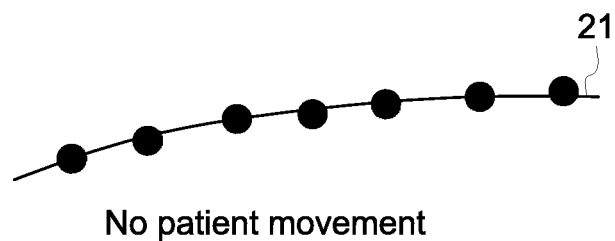
FIG. 2 is a schematic view of the positioning of the object of interest in successive scans when the position of the object of interest is not affected by patient movement according to an exemplary embodiment of the invention.

Referring to FIG. 2, a distinct feature 103 of the breast will project onto the detector at a different position for each different image, resulting in a projection path 20, because the x-ray source position is different for each image. Furthermore, a projection path 21 among all view angles generally follows a smooth trajectory for a tomosynthesis scan which is free of patient motion because of the way x-ray source motion is defined, e.g., in a controlled arc, and because x-ray exposures are taken in a temporally and spatially uniform manner. However, the projection of the feature will not follow a smooth trajectory if the patient moves during the scan.

Figure 3A:
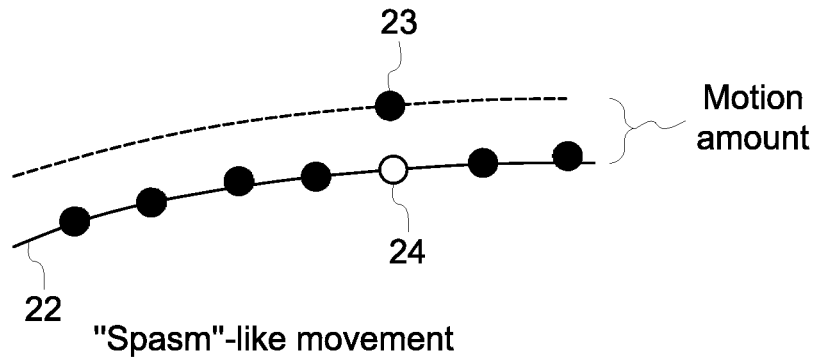
FIGS. 3A-3C are schematic views of the positioning of the object of interest in successive scans when the position of the object of interest is affected by patient movement of different types according to an exemplary embodiment of the invention.
Figure 3B:
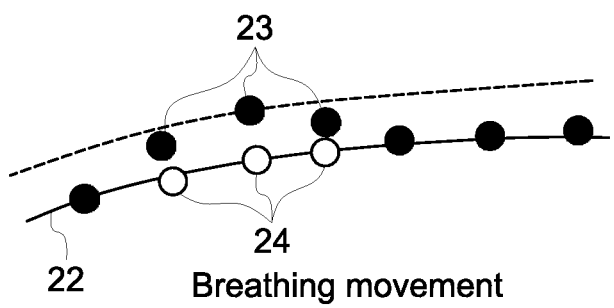
Figure 3C:
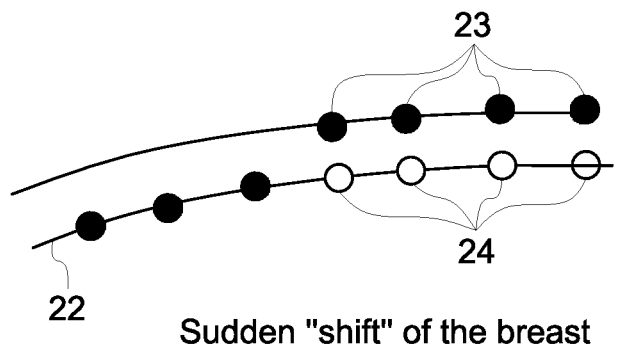

FIGS. 3A-3C illustrate different projection paths 22 where an image is affected by patient movement. In one image the actual position 23 of the object of interest or feature differs from the expected position 24 of the object of interest or feature. The difference between the actual position 23 and the expected position 24 is indicative of the magnitude of patient motion. There is also a defined direction or vector of the motion identified for the object of interest which can be utilized in the determination of the motion and type of motion of the patient during the scan. For example, if the motion of an object on interest in various images of a scan is repetitive in direction across multiple images, the motion may be caused by the breathing of the patient (FIG. 3B), which could necessitate a different response to the correction of the image(s) and/or the entire scan than a situation where the motion is present only in one or two images of the scan (FIG. 3A) or where the motion is constant in each image after a shift in the position of the patient (FIG. 3C). Consequently, features such as introduced markers, lesions, calcifications, masses and other artifacts in or on the x-rayed object can be used to detect patient motion and calculate an indication of the magnitude (severity) and direction of the motion, e.g., using a computer with processors, non-transitory memory and a computer program product which receives various inputs, performs various calculations, and provides outputs such as described in this application.

Additionally, some displacement may be expected due to motion of the x-ray source. However, the rate of change of displacement should define a smooth curve in the absence of patient motion. Consequently, the rate of change of displacement can also be used to detect patient motion.

For determining motion present in the images, any number of different methods for determining the presence of motion can be employed. In one exemplary embodiment, for automated motion detection, any calcifications and/or other object(s) of interest can be detected in the DBT images or projections, and the detected objects can be correlated at least between subsequent images or projection or within the whole series of projections. This step determines or locates an object or feature of interest in one projection and searches for it within a previous or subsequent projection in a determined neighborhood or area of the image/projection in which the object or feature expected to be located, where the neighborhood is selected to be large enough to model where the object can be located even if motion has occurred. The motion component can be measured comparing the expected position of the object or feature with the measured one. As disclosed in the '180 patent, previously incorporated herein by reference in its entirety for all purposes, once the object is located, in one exemplary embodiment the presence of patient motion and calculation of the magnitude and direction of that motion in an automated manner can be accomplished by fitting a $2^{nd}$ order curve to the locations/features of each image. The deviation of each location/feature from the expected location on the $2^{nd}$ order polynomial fitting curve is then calculated. The maximum deviation is recorded as the motion amount of the feature or object of interest at the analysis location. In another exemplary embodiment, motion can be detected by analyzing the distortion of the PSF (Point Spread Function) in reconstructed volumes. Calcification artifacts or other objects of interest are not aligned in case of motion of the patient.

In an alternative exemplary embodiment, this motion detection step can be done manually where the operator can use the system 200 to detect the motion of structures within the images or projections obtained by the system 200. In one exemplary embodiment this can be done by adding a visual reference, such as a vertical digital grid distorted/replaced to adapt to the system geometry, on top of the display of the acquired projections. With the images or projections displayed in this manner, it is easy for the operator to detect structures that are not aligned on the same line on successive projections and/or in a reconstructed volume.

Figure 4:
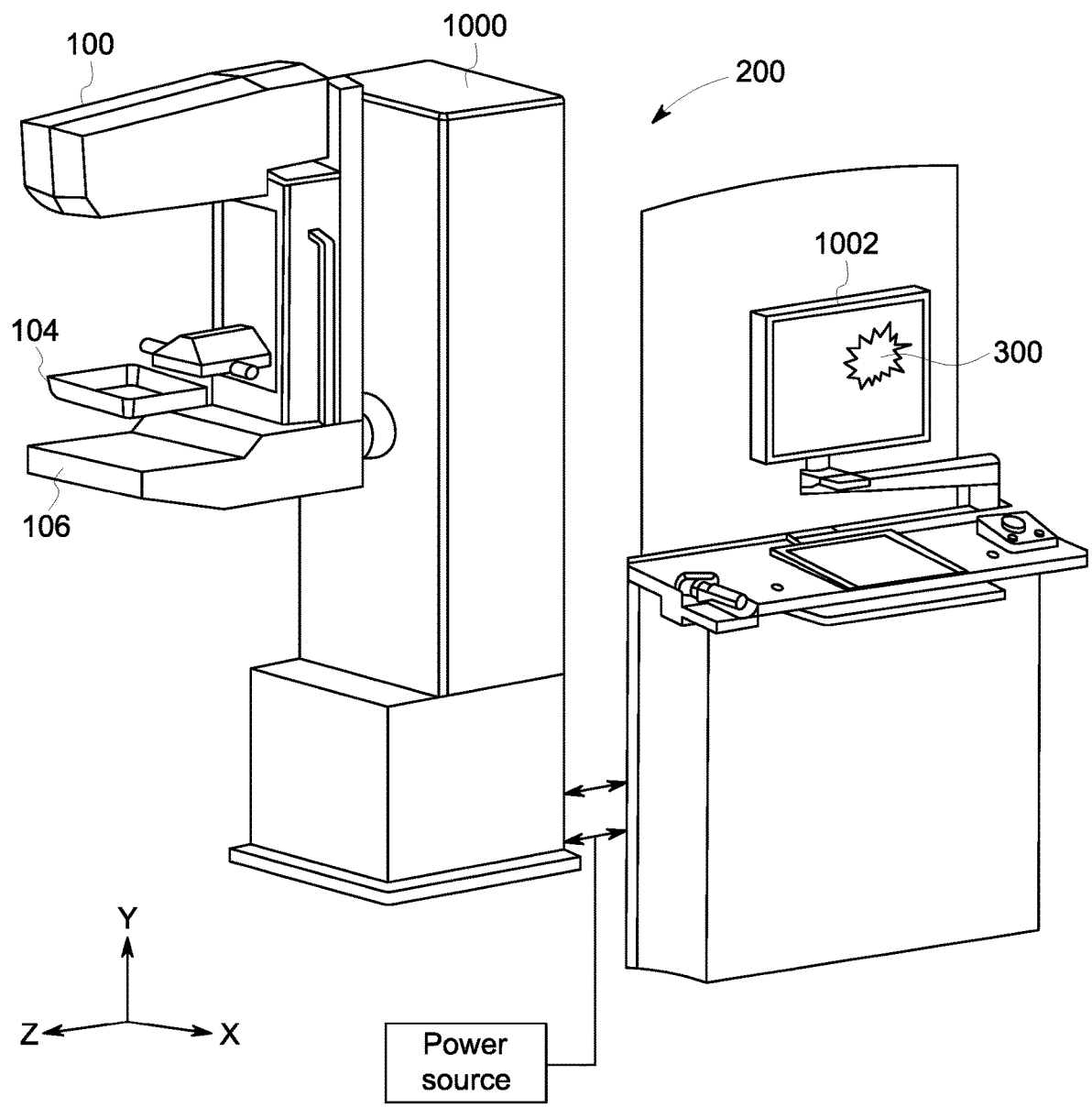
FIG. 4 is an isometric view of an imaging system used to perform the scan of the patient according to an exemplary embodiment of the invention.
Figure 5:
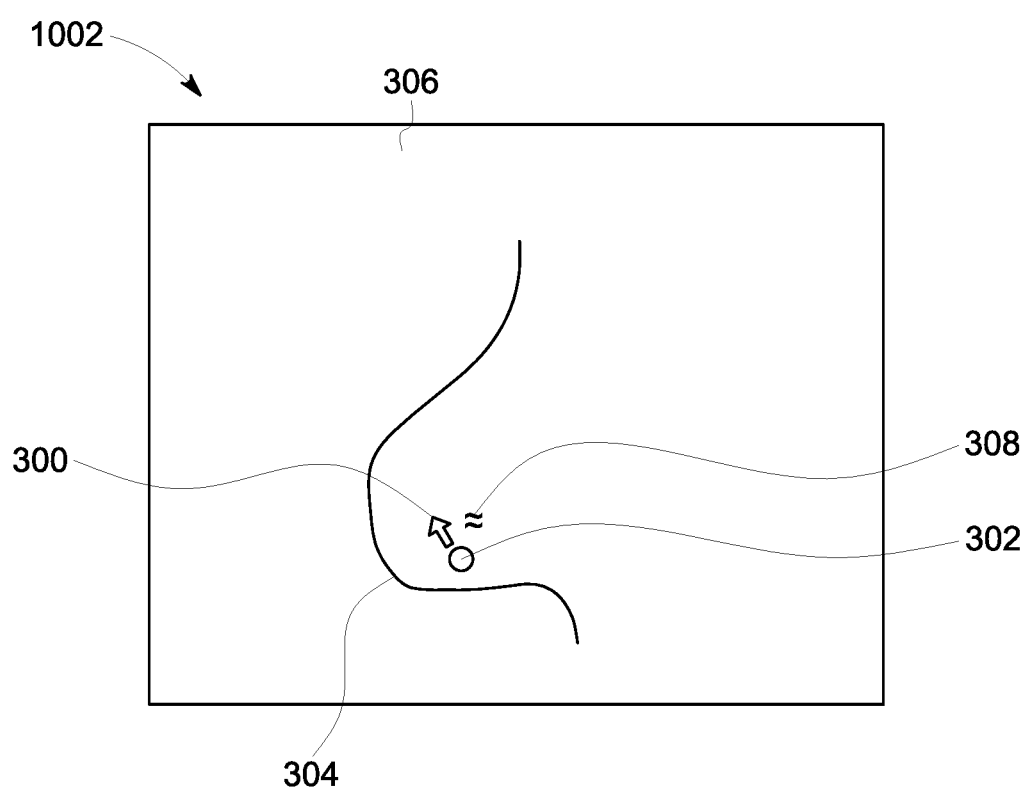
FIG. 5 is a schematic view of a method for detecting, quantifying and representing patient motion during a tomosynthesis scan according to an exemplary embodiment of the invention.

Using any manner of determining the presence of motion in the projections or images obtained by the system 200 or reconstructed volume(s) produced by the system 200, the location of regions or areas affected by motion can be highlighted in the projections or in the volume on the display 1002 (FIG. 4) with a motion marker 300, as shown in FIG. 5. This highlighting or motion marker 300 is positioned or overlaid directly on the image 306 and can be represented by geometric shapes, or other markers put around the degraded location/area 302 of the breast 304 in the image or volume, placing identifying vectors and/or colorization on the given area in the projections or volume, forming and placing a 2D or 3D map identifying the motion over the displayed projections, images or reconstructed volumes, or combinations thereof, among other suitable motion markers 300, which can optionally include other information or data 308 about the nature of the motion marker 300. The motion marker(s) 300 provides a visual and proportional representation to the operator of one or more of the amplitude of motion, direction of motion, probability of motion direction, and/or variation over time of the motion. In an exemplary embodiment of the representation of the motion, whether represented in real-time for a processed images obtained during the scan or on a reconstructed image or volume obtained after the scan has been completed, the motion marker 300 can be correlated to the displacement amount in selected units, e.g., in mm, where the displacement is the deviation of the feature 302 from the expected position. Such techniques will be readily apparent to those skilled in the art.

Figure 6:
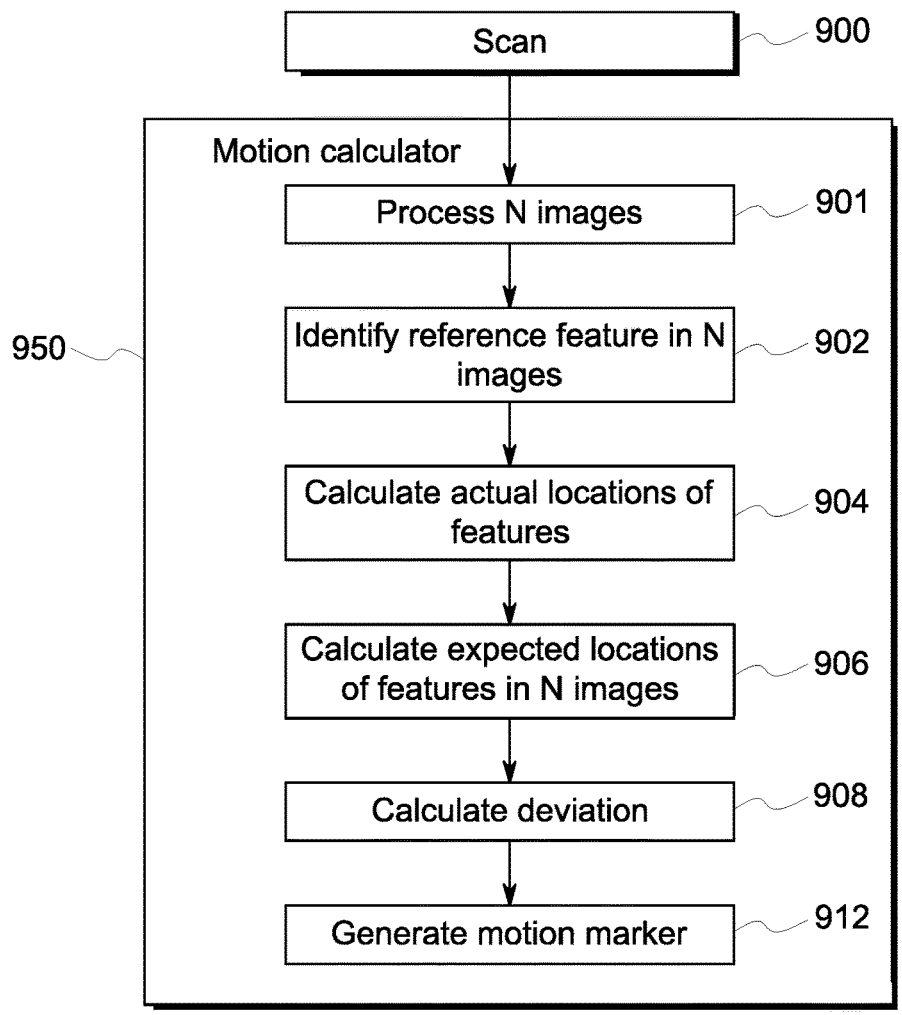
FIG. 6 is a schematic view of a method for displaying the representation of the patient motion according to an exemplary embodiment of the invention.

Referring to FIG. 6, a method of detecting and quantifying patient motion begins with a scan 900 by the system 200 (FIG. 4), an example of which is the Senograph Pristina 3D, manufactured by GE Healthcare, in which multiple images are obtained in time-series. The images are then transformed, reconstructed or otherwise processed to generate one or more images that can be utilized to detect motion as indicated by step 901. The motion detection may be, for example, obtained by comparison of the results obtained from a pair of successive processed images, another subset of images obtained in the entire scan 900, or from reconstructed slices or a reconstructed volume created from a number of the images in the scan 900. The next step 902 is to identify a reference feature within the image of the breast. The actual locations of the features associated with each of N images of the breast are then calculated in step 904. The expected locations of the features associated with the N images of the breast are then calculated in step 906 of all or a subset of images. Furthermore, the process may be iterative. For example, the number of images in the subset may be changed in different iterations. Also, different fitting models may be utilized in different iterations. Iteration may be stopped when predetermined conditions are satisfied. The deviation of each feature from the expected location in the N images is then calculated in step 908.

The process then generates a motion marker 300 based on the deviation determined across the analysis of the N image in step 912, where the motion marker 300 can provide information relating to the multiple aspects of the detected motion, including but not limited to the magnitude and direction of the motion detected for the feature or object of interest. The entire algorithm for calculating the motion marker 300 is identified as group 950.

Figure 7:
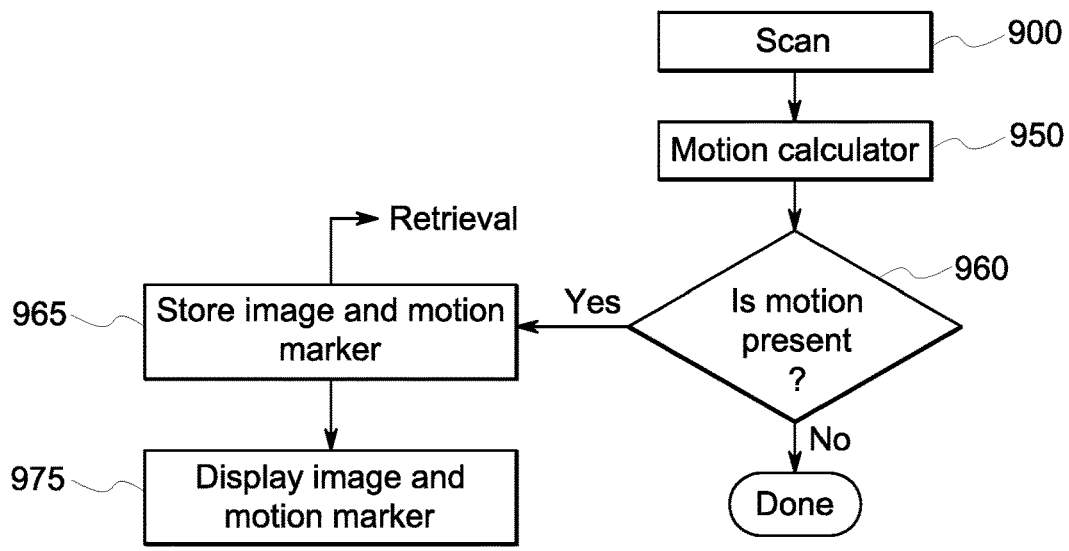
FIG. 7 is a schematic view of the presentation of motion markers representing the presence, magnitude and direction of motion in scan images according to an exemplary embodiment of the invention.

Referring to FIG. 7, the scan 900 is followed by the analysis of the motion calculator 950, as described with regard to FIG. 6. If no motion is detected, from decision block 960 the system 200 will stop the analysis for the selected images N and may subsequently initiate another analysis for a different set of images.

However, if motion has been detected by the system 200 as determined by the motion calculator 950, from decision block 960 the image set N and associated motion marker 300 are stored in step 965 and displayed or presented to the user in step 975. The presentation of the motion marker 300 provided to the technician may include initially displaying a signal, icon or other visual or auditory representation of patient motion on a user interface of the tomosynthesis system (FIG. 4), e.g., on the gantry 1000 or on a workstation 1002 coupled to the gantry for viewing by a radiologist. In addition, the motion marker 300 is presented on the display for the workstation 1002 in conjunction with the representation of the image(s) in which the motion occurred. The motion marker 300 not only indicates that motion has occurred but also provides information, either using the motion marker 300 and/or in conjunction with other information 308, regarding one or more aspects of the motion that has been detected in the image(s). The motion marker 300 provides this information by being displayed as an overlay cat the image(s) on the workstation 1002, whether the image(s) are a processed set of N images or reconstructed slices, slabs or volumes based on the processed set of N images, such as geometric shapes, or other markers put around the blurred or degraded location/area of motion in the image or volume, placing identifying vectors and/or colorization on or around the motion location(s) and/or area(s) in the projections or volume, forming and placing a 2D or 3D map proportionally identifying the location(s) and area(s) of motion over the displayed projections, images or reconstructed volumes, or combinations thereof, among other suitable motion markers 300.

In this manner, motion detection and associated display of a motion marker 300 indicative of patient motion and severity may be used to enhance the tomosynthesis system. For example, in response to a motion marker 300 illustrating in real-time the motion of the patient during the scan, the technician may immediately stop the acquisition before its end, to avoid useless dose exposure(s), and/or re-take the tomosynthesis images, perhaps before the patient is dismissed. A scan may be deemed acceptable by the operator if the motion marker 300 indicates some amount of patient motion has been detected, but of an amount that does not affect the quality of the images from the scan. Based on the information provided by the motion marker 300, the operator may also manually select images for removal from processing and reconstruction to improve the image quality of final reconstruction slices. The motion detection can take place in real time, or at some later time after the patient has left or the operator is finished with the procedure.

Instead of or in addition to the notification/highlighting of the degraded area using the motion marker(s) 300, the images could be corrected to make the object of interest impacted by motion correlated in the space, and therefore reconstructed correctly (e.g. without blur). This step can be done using standard rigid or non-rigid registration techniques. Additionally, the images or projections can be separated in two parts by isolating the signal component containing the objects of interest, e.g., calcifications from the rest of the breast, then reconstructing the unregistered projections without the objects or features of interest and by further reconstructing the registered object of interest separately and finally combining the two volumes.

It is envisioned that motion detection and quantification may be performed using reconstructed slice images although the above methods of tracking artifacts have described comparison of sequential projection images. In tomosynthesis reconstruction the projections images are summed after shifting and transforming one relative to another in a specific way (referred as component images) to produce a reconstruction slice that reinforces the spiculated lesion object located at the height of that slice in a breast and reduces the contrast of other objects located away from the slice by blurring them out. One technique for performing motion detection and quantification using reconstructed slice images is to compare individual locations in the component images with the reconstructed slice image at the height at which the feature is in focus. The difference between locations in each individual component image versus the location in the reconstruction slice is used as the displacement in the calculations described above. Another example is to utilize a slice where the selected feature is out of focus. In such a case the locations of the selected feature appears as a trajectory cluster (epi-polar curve), so the analysts is performed by finding the location of each member of the cluster individually, and then finding the expected location of that member. Accordingly the manual visual confirmation method can also be applied to review tomosynthesis reconstruction slices by co-displaying reference lines superimposed on display monitor. Such alternative embodiments are therefore within the scope of the present invention. Furthermore, although the above description has dealt largely with detecting patient motion during tomosynthesis imaging for the purpose of predicting image quality, it can easily be appreciated how the principles of the present invention may be extended beyond the tomosynthesis modality to any imaging which acquires at least two images of an object over an extended tune period. Such modalities include, but are not limited to, Computed Tomography (CT) scans, Positron Emission Tomography (PET) scans, Single Photon Emission Computed Tomography (SPECT) scans, ultrasound image acquisition, contrast enhanced imaging, and Magnetic Resonance Imaging (MRI). Thus, the present invention may be used for any time-series of image acquisition system to identify any abnormal changes between sequenced images attributable to patient motion during the acquisition. Motion detection and analysis can also be included as pan of system QC test; if mechanical component is malfunctioning, it would generate a non-zero motion score from phantom scan and help identify the problem in the mechanical system.

In addition, after presentation of the image 306 and associated motion marker 300 on the display for the workstation 1002 in conjunction with the representation of the image(s) in which the motion occurred, the operator can select the marker 300 in order to focus the image 306 on the area 302 of the image 306 in which the motion occurred and/or was detected. This process can be similar to that described in US Patent Application Publication No. US2016/0183901 entitled Method And System for Tomosynthesis Projection Images Enhancement, the entirety of which is expressly incorporated herein by reference for all purposes. In this exemplary embodiment, after generating the 3D motion marker or map 300 indicating the amount and orientation of the motion detected in the images 306 of the breast 304, the system 200 can generate a 2D motion map or marker 300 by altering the 3D map following a geometry defined by a processed projection image 306, where the placement of the 2D marker/map in the 2D image is located at the location of maximum detected motion maximum along the projection ray through the 3D map/marker 300.

Once generated, the 2D marker/map is overlayed on the 2D projection or image 306 when displayed to the operator to indicate the position of movement detected in the breast 304 during the scan. In reviewing the 2D image 306, should the operator desire to see the 3D image and associated motion marker 300 to access additional information regarding the motion that occurred, the operator can select the 2D marker 300 or the area 302 in which the marker 300 is positioned in the 2D projection 306 and the system 200 will shift the display to present the area 302 in the reconstructed 3D image 306 corresponding to the maximum motion value of the 3D map/marker 300 on the display. In this manner, the system 200 enables the operator to more quickly review the 2D projections/images 306 and the motion information presented thereon via marker 300. Then, if the operator wishes to obtain more information on the magnitude of motion represented in a particular 2D image 306 by the marker 300, the operator can select that marker 300 to gain access to the reconstructed image 306 containing additional 3D information regarding the motion and the affected area 302 in the 3D image 306.

Accordingly, a system, apparatus, method and computer program have been described for detecting and quantifying motion of an object or a component of the motion of the object by evaluating displacement of a feature within a series of images acquired over a time period. The feature may be, without limitation, a skin line, internal edge line, internal object such as calcification, lesion, mass or other object, or an external marker. Any one of a variety of imaging modalities may be used, and the quantified motion may be displayed in any variety of manners, including but not limited to on the acquisition device, on technologist workstation, and in a dicom header. The quantified motion may be used to generate a motion score, prompt re-acquisition of images, as an input to an image processing stage of a reconstruction algorithm, and as an input to a CAD processing system.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus comprising:
an image acquisition system that generates a plurality of images of an imaging target of an object in a time series during a scan;
an image processor that processes the plurality of images to generate processed images, wherein the processed images are at least one of projection images or reconstructed images;
a computer which is configured to detect and quantify motion of the imaging target in the processed images during the scan by comparing an actual location of at least one object of interest in each processed image with an expected location of the at least one object of interest derived from a set of the processed images,
wherein the computer is further configured to correct the processed images in which the motion of the imaging target was detected by:
isolating an image component of the processed images containing the at least one object of interest;
reconstructing the processed images without the image component;
reconstructing the image component; and
combining the reconstructed images and the reconstructed image component to form corrected processed images.

2. The apparatus of claim 1 wherein the at least one object of interest is an intrinsic marker of the object.

3. The apparatus of claim 1 wherein the image acquisition system is configured to acquire the plurality of images using a process selected from a group consisting of tomosynthesis, computed tomography (CT), positron emission tomography (PET), single photon emission computed tomography (SPECT), ultrasound, and magnetic resonance imaging (MRI).

4. The apparatus of claim 1 wherein the image acquisition system is a digital breast tomosynthesis system.

5. The apparatus of claim 1 wherein the computer is configured to quantify the motion based on change of displacement or rate of change of displacement of the at least one object of interest.

6. The apparatus of claim 1 wherein the computer is configured to quantify the motion based on maximum displacement of the at least one object of interest.

7. A method comprising:
generating a plurality of images of an imaging target of an object in a time series during a scan;
processing the plurality of images to generate processed images, wherein the processed images are at least one of projection images and reconstructed images;
using a computer, detecting and quantifying motion of the imaging target of any magnitude in the processed images during the scan by comparing an actual location of at least one object of interest in each processed image with an expected location of the at least one object of interest derived from a set of the processed images, wherein the at least one object of interest is an intrinsic marker of the object;
correcting the processed images in which the motion was detected;
wherein correcting the processed images includes:
isolating an image component of the one or more processed images containing the at least one object of interest;
reconstructing the processed images without the image component; reconstructing the image component; and
combining the reconstructed images and the reconstructed image component to form corrected processed images.

* * * * *